US00PP31854P3

(12) United States Plant Patent
Berry

(10) Patent No.: US PP31,854 P3
(45) Date of Patent: Jun. 9, 2020

(54) ***HIBISCUS* PLANT NAMED 'JBG 14003'**

(50) Latin Name: *Hibiscus rosa-sinensis*
Varietal Denomination: JBG 14003

(71) Applicant: Capstone Plants, Inc., Grand Saline, TX (US)

(72) Inventor: James Berry, Edgewood, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 15/998,303

(22) Filed: Aug. 2, 2018

(65) Prior Publication Data

US 2019/0045688 P1 Feb. 7, 2019

Related U.S. Application Data

(60) Provisional application No. 62/605,169, filed on Aug. 3, 2017.

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC . A01H 5/02; A01H 6/60; A01H 6/608; A01H 5/00
See application file for complete search history.

(56) References Cited

PUBLICATIONS

Baumle. A taste of the tropics, Progress Newspaper 2017, retrieved on May 20, 2019, retrieved from the Internet at https://progressnewspaper.org/PrintArticle.aspx?aid=195057&uid=ae42c8f9-6283-456e-8db0-379fbe2ec82a, 2 pp. (Year: 2017).*
Hill Red pineapple, Ananas 'Pacifico', Hidden Hills Gardfen posted Feb. 19, 2016 retrieved on Sep. 16, 2019, retrieved from the Internet at http://hiddenhillsgarden.com/blog/?p=5007, 11 pp. (Year: 2016).*
Hollywood *Hibiscus*. Social Butterfly Hollywood *Hibiscus* 2018, retrieved on May 20, 2019, retrieved from the Internet at https://www.hollywoodhibiscus.com/portfolio/hollywood-hibiscus-social-butterfly, 4 pp. (Year: 2018).*

* cited by examiner

*Primary Examiner* — June Hwu
(74) *Attorney, Agent, or Firm* — The Webb Law Firm

(57) ABSTRACT

A new and distinct *Hibiscus* plant having yellow colored flowers with a red-toned throat that last for several days on the plant over a long flowering season.

1 Drawing Sheet

Botanical classification: *Hibiscus rosa-sinensis.*
Varietal denomination: 'JBG 14003'.

BACKGROUND OF THE INVENTION

The present invention comprises a new and distinct *Hibiscus* plant having the varietal name 'JBG 14003'. The new variety is the result of a planned breeding program with the purposes of developing *Hibiscus rosa-sinensis* plants that exhibit pathogen resistance, multi-day flowers with unique coloration, and possess desirable production traits. 'JBG 14003' is the result of a cross conducted in Grand Saline, Tex. between *Hibiscus rosa-sinensis* varieties 'JBG 8413-4' (female parent, unpatented) and 'JBG 782' (male parent, unpatented). The new variety was selected in November of 2013 in Grand Saline, Tex. and the first asexual reproduction of the new variety was conducted by semi-mature, softwood cuttings in October of 2014 in Grand Saline, Tex. 'JBG 14003' has been trial and field tested and has been found to retain its distinctive characteristics and remain true to type through successive propagations. The present invention has not been evaluated under all possible environmental conditions. The phenotype may vary with variations in environment without a change in the genotype of the plant.

'JBG 14003' is similar to its female parent in having white highlights on yellow colored, overlapping petals with a red-toned throat, but differs from its female parent in having smaller flowers with a darker red colored flower throat and an increased bud count. 'JBG 14003' is similar to its male parent in having a dark colored throat and overlapping petals with yellow colored margins, but differs from its male parent in having smaller flowers with white colored highlights across the petals and an increased bud count.

When 'JBG 14003' is compared to *Hibiscus rosa-sinensis* variety 'JBG 14002' (U.S. Plant Pat. No. 30,580), both varieties exhibit overlapping petals and a dark colored flower center. However, the dark coloration of the flower center of 'JBG 14003' extends upwards and fades through the throat of the flower, while such extension is not present with 'JBG 14002'.

The following traits distinguish 'JBG 14003' as a new and distinct cultivar from other *Hibiscus* varieties known to the breeder:

1. Yellow colored flowers with a red-toned throat;
2. Overlapping flower petals;
3. Resistance to bacterial leaf spot (*Pseudomonas* spp.); and
4. Multi-day flowers.

DESCRIPTION OF THE DRAWING

The accompanying photographic image illustrates the new variety at approximately one year of age, with the colors being as nearly true as is possible with color illustrations of this type:

FIG. 1 illustrates a close-up view of a flower of the new variety.

DESCRIPTION OF THE PLANT

The following detailed description sets forth the characteristics of the new variety. The color readings and measurements were taken in the summer in Grand Saline, Tex. under natural light on approximately one year old, growing plants in 24.0 cm diameter containers. Color references are primarily to The 1995 R.H.S. Colour Chart of The Royal Horticultural Society of London, 3rd Edition, except where general color terms are used.

PLANT

Time to initiate roots: About 42 days at an average of 24° C.
Time to develop roots: About 50 days at an average of 24° C.
Time to produce a finished flowering plant from a rooted cutting: About 30 weeks in a 24.0 cm diameter container.
Specific disease/pest resistance: Resistance to bacterial leaf spot (*Pseudomonas* spp.).
Heat/cold tolerance: Nothing unusual noted to date; not hardy below 33° F.
Drought tolerance: Nothing unusual noted to date.
Plant:
- *Type*.—Tropical, ornamental shrub.
- *Habit*.—Upright.
- *Height*.—150.0 cm at maturity.
- *Spread*.—120.0 cm at maturity.
- *Vigor*.—Strong.

Rooting vigor: Strong.
Stem:
- *Number per plant*.—12.
- *Length*.—Ranging from 38.0-69.0 cm.
- *Width*.—6.0-7.0 mm.
- *Texture*.—Immature: Smooth. Mature: Vertically ridged.
- *Strength*.—High.
- *Branch number*.—High.
- *Internode length*.—3.5-4.0 cm.
- *Color*.—Immature: 144B. Mature: 199B.
- *Stipules*.—Number per node: 2. Shape: Linear. Length: 8.0 mm. Width: 1.0 mm. Surface texture: Smooth. Apex: Acuminate. Base: Linear. Margin: Entire. Color: 143C.

Foliage:
- *Arrangement*.—Alternate; simple.
- *Size of leaf*.—Length: 10.0 cm. Width: 7.0 cm.
- *Shape of leaf* (*generally*).—Ovate.
- *Shape of apex*.—Acute.
- *Shape of base*.—Rounded.
- *Texture* (*both surfaces*).—Slightly tomentose.
- *Margin type*.—Slightly crenate.
- *Color*.—Young leaves: Upper surface: 137C. Lower surface: 137D. Mature leaves: Upper surface: 137A. Lower surface: 137B.
- *Veins*.—Venation type: Pinnate. Color: Upper surface: 137C. Lower surface: 138B.
- *Petiole*.—Length: 3.0 cm. Diameter: 3.0 mm. Texture: Smooth. Color: 144A.

FLOWERS

Buds (described approximately 1 day from opening):
- *Shape*.—Oblong.
- *Diameter*.—2.0 cm.
- *Length*.—6.0 cm.
- *Color*.—11A.

Natural flowering season: From spring through fall in Grand Saline, Tex.
Flower type and habit: Single, with overlapping petals.
Fragrance: None observed.
Flowers (described on the first day of opening):
- *Number per stem*.—1.
- *Overall depth*.—8.0 cm.
- *Overall diameter*.—12.0 cm.
- *Shape*.—Rotate; regular.
- *Lastingness*.—3 days on the plant.
- *Petals*.—Number: 5. Arrangement: Simple. Length: 7.0 cm. Width: Apex: 6.0 cm. Base: 2.0 cm. Shape: Obovate. Apex: Obtuse. Base: Cuneate. Margin: Slightly ruffled. Incisions: Absent. Texture/appearance: Upper surface: Smooth. Lower surface: Slightly pubescent. Color: When opening and fully opened: Upper surface: 9A at the apex to 23A then to 46A at 4.0-6.0 cm in diameter at the throat and an eye zone extension (petal venation) of 63C extending 1.0-2.0 cm beyond the 63C eye. Lower surface: 8B at the apex to 54C at the base.
- *Calyx*.—Form: Fused. Overall length: 3.0 cm. Overall diameter: 1.1 cm. Sepals/calyx lobes: Number: 5. Shape: Lanceolate. Apex: Acute. Margin: Entire. Texture: Slightly pubescent. Color: Outer surface: 144A. Inner surface: 144A.
- *Epicalyx*.—Length: 1.2 cm. Width: 4.0 mm. Texture: Smooth. Color: 146B.
- *Bracts*.—Not present.
- *Peduncle*.—Length: 7.0 cm. Diameter: 3.0 mm. Strength: Strong. Angle: 30°. Texture: Smooth. Color: 144A.

Reproductive organs:
- *Gynoecium*.—Pistils: Number: 1. Length: 8.0 cm. Stigma: Number: 5. Shape: Round. Length: 9.0 mm. Diameter: 1.0 mm. Color: 46B. Style: Length: 6.5 cm. Width: 4.0 mm. Color: 46B at the base, changing to 63C then to 9D at the apex just below the stigma. Ovary: Shape: Ovate. Length: 1.2 cm. Width: 1.0 cm. Color: 3C.
- *Androecium*.—Stamens: Number: 88. Position: Just below the stigma on the style. Anther: Shape: U-shaped. Diameter: 2.0 mm. Color: 12A. Filament: Length: 6.0 mm. Width: 1.0 mm. Color: 155B at the apex to 55B at the base. Pollen: Color: 12A. Amount (generally): Moderate.

SEEDS

Seeds:
- *Number*.—From 0 to 20.
- *Color*.—200C.
- *Length*.—5.0 mm.
- *Width*.—5.0 mm.

I claim:

1. A new and distinct variety of *Hibiscus* plant, as is herein illustrated and described.

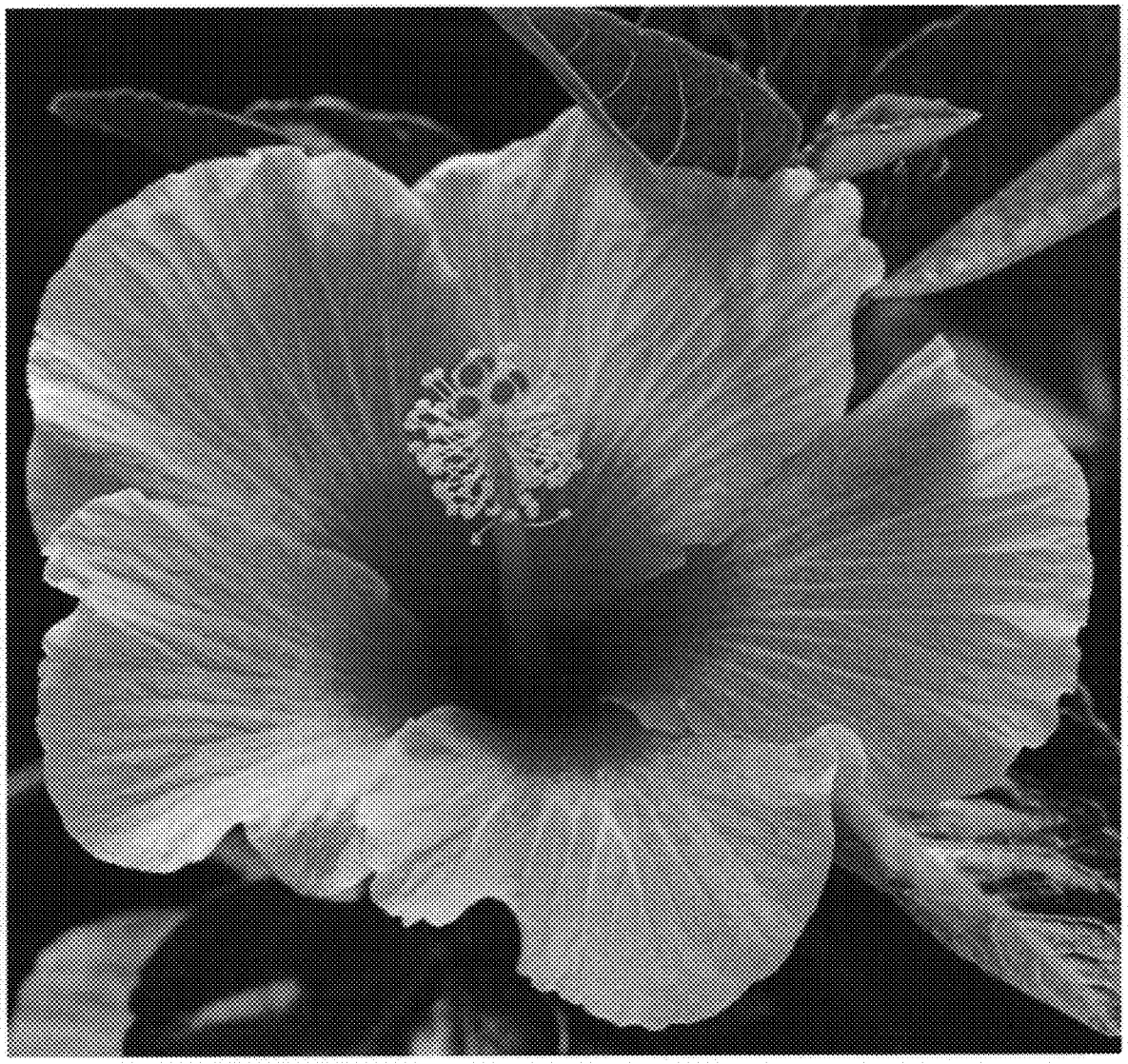

* * * * *